(12) United States Patent
Burchiel et al.

(10) Patent No.: US 10,363,421 B2
(45) Date of Patent: *Jul. 30, 2019

(54) ELECTRODE PLACEMENT AND STIMULATION BASED ON BROWN ADIPOSE TISSUE TEMPERATURE

(71) Applicant: OREGON HEALTH & SCIENCE UNIVERSITY, Portland, OR (US)

(72) Inventors: Kim Burchiel, Portland, OR (US); Christopher J. Madden, Portland, OR (US); Shaun F. Morrison, Banks, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/943,492

(22) Filed: Apr. 2, 2018

(65) Prior Publication Data

US 2018/0221665 A1  Aug. 9, 2018

Related U.S. Application Data

(63) Continuation-in-part of application No. 15/465,461, filed on Mar. 21, 2017, now Pat. No. 9,962,542, which is a continuation of application No. 14/641,770, filed on Mar. 9, 2015, now Pat. No. 9,604,060.

(Continued)

(51) Int. Cl.
| | |
|---|---|
| *A61N 1/36* | (2006.01) |
| *A61B 5/00* | (2006.01) |
| *A61B 5/01* | (2006.01) |
| *A61N 1/05* | (2006.01) |

(52) U.S. Cl.
CPC ............ *A61N 1/36085* (2013.01); *A61B 5/01* (2013.01); *A61B 5/4836* (2013.01); *A61N 1/36139* (2013.01); *A61B 2562/0271* (2013.01); *A61N 1/0534* (2013.01); *A61N 1/36117* (2013.01)

(58) Field of Classification Search
USPC ................................................... 607/44–45
See application file for complete search history.

(56) References Cited

U.S. PATENT DOCUMENTS

| | | | |
|---|---|---|---|
| 2010/0312295 A1* | 12/2010 | Vase | A61N 1/0551 607/2 |
| 2011/0137371 A1* | 6/2011 | Giftakis | A61N 1/36139 607/45 |

\* cited by examiner

*Primary Examiner* — Nicole F Lavert
*Assistant Examiner* — Nicole F Johnson
(74) *Attorney, Agent, or Firm* — Schwabe, Williamson & Wyatt, P.C.

(57) ABSTRACT

Systems and methods for spinal cord electrode placement and spinal cord stimulation their use for treatment of conditions such as obesity are disclosed. In one example approach, during placement of a spinal cord stimulating electrode in a target region of the brain of a patient, a temperature of brown adipose tissue may be monitored, e.g., via a supraclavicular temperature sensor implanted in the patient, and used to identify an optimal location of electrode stimulation which causes an increase in BAT temperature. Additionally, BAT temperature measurements may be used to provide regulated closed-loop control to increase efficiency of spinal cord stimulation while reducing energy consumption of the pulse generator. Further, core temperature measurements may be obtained from the electrode in the spinal cord and used to adjust spinal cord stimulation.

20 Claims, 9 Drawing Sheets

Related U.S. Application Data

(60) Provisional application No. 61/951,306, filed on Mar. 11, 2014.

ELECTRODE PLACEMENT AND STIMULATION BASED ON BROWN ADIPOSE TISSUE TEMPERATURE

CROSS REFERENCE TO RELATED APPLICATIONS

This application is a Continuation-in-part Application of and claims priority to U.S. patent application Pub. No. 2017/0209687, filed on Mar. 21, 2017, which is a Continuation Application of and claims priority to U.S. patent application Pub. No. 2015/0258339 (now U.S. Pat. No. 9,604,060), filed on Mar. 9, 2015, which claims priority to U.S. Provisional Patent Application No. 61/951,306, filed on Mar. 11, 2014, the disclosures of which are hereby incorporated by reference in their entireties.

FIELD

The present disclosure relates to the field of central nervous system stimulation, and, more specifically, to systems and methods for spinal cord electrode placement and stimulation based on brown adipose tissue temperature.

BACKGROUND

Obesity is a growing global health problem frequently intractable to current treatment options. For example, lifestyle changes such as exercising and limiting dietary intake may not be successful at controlling obesity, e.g., due in part to compensatory responses that reduce metabolism in response to dietary restriction. Medical interventions such as appetite suppressant medications may be only marginally successful in assisting weight loss and invasive surgical interventions such as gastric bypass surgery have increased risks. Thus, it is desirable to provide alternative interventions that can successfully control weight gain and appetite with reduced risks.

Deep brain stimulation (DBS) in select brain regions has provided therapeutic benefits for otherwise-treatment-resistant movement disorders such as Parkinson's disease, essential tremor, and dystonia. Treatment with DBS has also been attempted for a variety of other clinical indications such as depression, obsessive-compulsive disorder, and epilepsy. Given the success of DBS in these clinical efforts, other indications for which there is currently little effective therapy are being evaluated preclinically, for eventual clinical use. Obesity may be one such indication.

DBS involves implanting slender leads tipped with electrical contacts at a specific location in a target region of the brain of a patient. The electrodes are designed to nondestructively deliver mild electric pulses to the specific location. The leads are connected to an implanted, compact, battery-operated pulse generator in a fashion similar to a heart pacemaker. DBS leads are placed in the brain according to the type of symptoms to be addressed and thus correct placement of the stimulating electrode is essential for the success of these approaches.

SUMMARY

The present disclosure is directed to systems and methods for deep brain electrode placement and deep brain stimulation (DBS) for treatment of obesity in patients. In one example approach, during placement of a deep brain stimulating electrode in a target region of the brain of a patient, the temperature of brown adipose tissue (BAT) may be monitored, e.g., via a supraclavicular temperature sensor, and used to identify an optimal location for delivery of DBS which causes an increase in BAT temperature.

As used throughout the present disclosure, the terms "brown adipose tissue" and "BAT" may be used to indicate any suitable inducible adipose tissue such as "classical" brown adipose tissue and other classifications of inducible brown adipose tissue such as beige, brown in white (brite), b/b, etc.

Increases in BAT temperature are indicative of an upregulation of thermogenesis in BAT. Thus, identifying an optimal location for electrode stimulation in a target region of the brain based on a measured increase in BAT temperature may provide a real-time functional assessment to accurately target DBS leads in a location associated with metabolism. Because it provides a direct measure of the effectiveness of the stimulation for acutely driving the effector tissues that are believed to contribute to the desired endpoint, such an approach may provide an increased electrode placement accuracy especially in conjunction with anatomical localization approaches which rely on imaging assistance such as magnetic resonance imaging (MM), computed tomography (CT), or indirect targeting methods such as microelectrode recording (MER). Further, approaches which rely on microelectrode recording (MER) for electrode placement utilize specialized equipment and expertise, demand dedicated intraoperative time to perform the recordings, and in most cases mandate that procedures are performed on awake patients under local anesthesia. Thus, placement of the electrode based on BAT temperature measurements may be performed at reduced cost compared to approaches which rely solely on MER, and potentially can be performed on patients under general anesthesia.

Ultimately, BAT temperature monitoring may be used to provide regulated closed-loop control to increase both efficiency and control of DBS while reducing energy consumption of the implanted pulse generator. In particular, after a DBS electrode is secured for DBS delivery to an optimal location in a target region of the brain of a patient, BAT temperature measurements may be provided as feedback to the pulse generator to control when DBS is activated and when DBS is deactivated in order to maintain a desired amount of active metabolism in the BAT. For example, DBS may be delivered to the target region of the brain via the electrode when the BAT temperature is less than a predetermined BAT temperature threshold and discontinued when the BAT temperature is greater than or substantially equal to the predetermined BAT temperature threshold.

Such an approach exploits a direct connection between BAT activation and brain stimulation to adjust delivery of DBS to the target region of the brain in real-time and thereby may preserve energy stored in the pulse generator, e.g., may extend the life of a battery within the pulse generator, while reducing occurrences of brain adaptation and resistance to the therapy. In particular, previous approaches provide continuous stimulation without monitoring functional responses of the DBS treatment in real-time and therefore may waste energy and increase occurrences of resistance to DBS therapy. For example, in such approaches, constant DBS may lead to brain accommodation to the DBS such that effectiveness of the DBS is reduced.

Additionally, in some examples, core brain temperature measurements may be obtained from the DBS electrode, e.g., via a temperature sensor integrated with the electrode, in order to monitor core temperature in the brain and adjust DBS accordingly. For example, in response to core temperature measured at the electrode increasing above a core temperature threshold, delivery of DBS via the electrode may be discontinued until the core temperature falls below the core temperature threshold. In this way, core temperature may be monitored within the brain at the electrode to provide a fail-safe mechanism during DBS.

Such methods and systems for DBS based on BAT temperature measurements may increase accuracy of electrode placement and provide accurate and efficient DBS for the treatment of obesity. Such approaches may additionally be used to treat hypertension, a common co-morbidity of obesity, and may be applied to other indications which could benefit from DBS treatment. For example, since BAT takes up glucose when activated, BAT activation via DBS as described herein may lead to decreases in hyperglycemia to potentially resolve diabetes mellitus.

The present disclosure is directed to methods for placement of a spinal cord stimulation electrode and regulation of spinal cord stimulation in a patient. The methods include: initially inserting a spinal cord stimulation electrode in a spinal cord region; delivering spinal cord stimulation directly via the spinal cord stimulation electrode directly to a first location in the target region by positioning the spinal cord stimulation electrode in the first location in the target region of the spinal cord in response to the initial insertion of the electrode to the target region; receiving temperature measurements from a brown adipose tissue temperature sensor; in response to an increasing brown adipose tissue temperature condition, outputting an indication to secure the spinal cord stimulation electrode for delivery of spinal cord stimulation directly to the first location; and in response to a non-increasing brown adipose tissue temperature condition, outputting an indication to adjust the spinal cord stimulation electrode by positioning the spinal cord stimulation electrode in an adjusted location in the target region until an increasing brown adipose tissue temperature condition occurs during delivery of spinal cord stimulation directly to the adjusted location in the target region, and then outputting an indication to secure the spinal cord stimulation electrode for delivery of spinal cord stimulation directly to the adjusted location.

The present disclosure is directed to a spinal cord stimulation system. The spinal cord stimulation system includes: an implantable pulse generator, the pulse generator comprising: an implantable housing; a battery within the housing; and a controller within the housing; an electrode coupled to the pulse generator; and a supraclavicular brown adipose tissue temperature sensor coupled to the pulse generator; wherein the controller is configured to: deliver spinal cord stimulation directly via the electrode directly to a first location in a target region of the spinal cord in response to an initial insertion of the electrode to the first location by positioning the electrode in the first location in the target region of the spinal cord in response to the initial insertion of the electrode to the target region; receive temperature measurements from the supraclavicular brown adipose tissue temperature sensor; in response to an increasing brown adipose tissue temperature condition, output an indication to secure the electrode for delivery of spinal cord stimulation directly to the first location; and in response to a non-increasing brown adipose tissue temperature condition, output an indication to adjust the electrode by positioning the electrode in an adjusted location in the target region until an increasing brown adipose tissue temperature condition occurs.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

The following detailed description is directed to systems and methods for deep brain electrode placement and deep brain stimulation (DBS) for treatment of patients. In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The terms "coupled" and "connected," along with their derivatives, may be used. It should be understood that these terms are not intended as synonyms for each other. Rather, in particular embodiments, "connected" may be used to indicate that two or more components are in direct physical or electrical contact with each other. "Coupled" may mean that two or more elements are in direct physical or electrical contact. However, "coupled" may also mean that two or more elements are not in direct contact with each other, but yet still cooperate, communication, or interact with each other.

Figure 1:
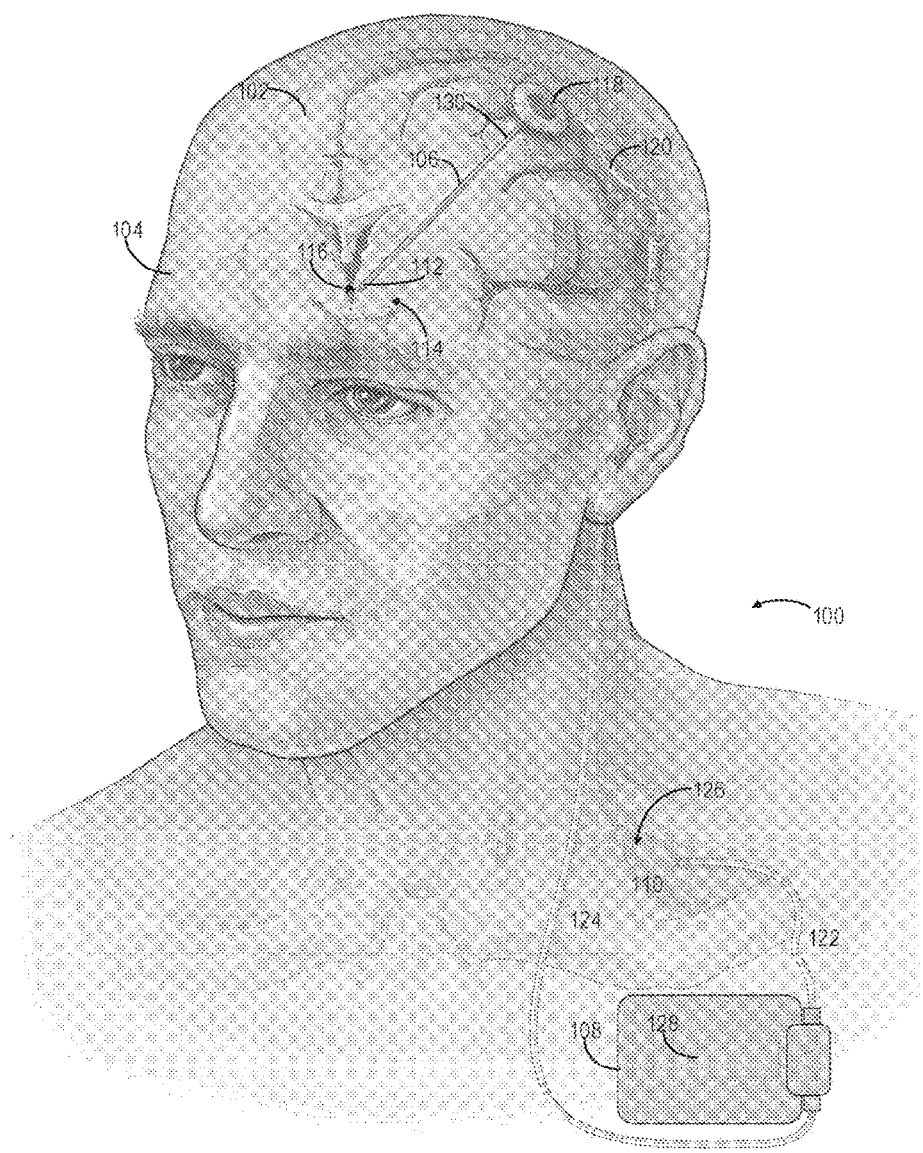
FIG. 1 shows an illustration of a deep brain stimulation system implanted in a patient in accordance with the disclosure.

FIG. 1 shows an illustration of an example DBS system 100 implanted in a patient 104. DBS system 100 includes an implantable neurostimulator or pulse generator 108. The pulse generator 108 includes a control unit or controller 128 and may be implanted within the patient's body, e.g., in a region 124 beneath the clavicle.

DBS system 100 includes an electrode 106 which can be implanted in the brain 102 of patient 104. A tip 112 of the electrode may be positioned at or near a location 116 in a target region 114 of the brain, where the target region is chosen based on the type of symptoms to be addressed by DBS. In embodiments, the electrode 106 may comprise a lead or wire, e.g., a coiled wire, and may include any suitable number of electrode contacts composed of any suitable material at or adjacent to the tip 112 of the electrode. For example, an electrode may comprise two or four platinum iridium electrode contacts at or near the tip 112 of the electrode.

The electrode 106 may be coupled to the pulse generator 108 via an electrode extension line 120. For example, the electrode extension line 120 may comprise insulated wires, e.g., insulated in polyurethane, that run from the head of the patient, down the side of the neck, behind the ear of the patient to the pulse generator 108 which may be placed in region 124 subcutaneously below the clavicle or, in some cases, the abdomen. In other embodiments, the electrode may be coupled to the pulse generator via a wireless connection such as Bluetooth® or other wireless communication system.

In some embodiments, electrode 106 may comprise a thermode configured to cause a temperature change at a location in a target region of the brain. In such embodiments, performing DBS with the thermode may comprise delivering a cold stimulus to the target region of the brain, e.g., decreasing the temperature by a predetermined amount via activation of the thermode. Decreasing temperatures of a target region of the brain via a thermode may lead to an increase in thermogenesis of BAT and therefore may be used instead of or in addition to an electrode which delivers electrical impulses to a target region of the brain in the treatment of various conditions such as obesity. For example, a thermode may be used to deliver DBS to the preoptic region of the hypothalamus to target temperature sensitive cells.

The pulse generator 108 may comprise a battery-powered neurostimulator encased in a housing composed of a suitable implantable material such as titanium. The pulse generator 108 is configured to send electrical pulses to the brain via electrode 106 to alter neural activity at the target site 114 in the brain. In some examples, the pulse generator may be calibrated by a neurologist, nurse, clinician, or trained technician to optimize symptom suppression and control side-effects, e.g., by adjusting various DBS parameters. Further, as described in more detail below, in some examples DBS parameters may be adjusted based on various functional assessments measured during delivery of DBS to the target region of the brain. In some embodiments, the neurostimulator may be powered by wireless power transfer (WPT). Wireless power transfer encompasses any method of powering a device at a distance without the use of solid wires. Such methods include inductive coupling, resonant inductive coupling, or capacitive coupling. In such embodiments, the batteries for the neurostimulator are provided in a housing on the outside of the body.

As remarked above, DBS in select brain regions may be used in the treatment of various conditions including obesity, e.g., for body weight reduction. The inventors herein have recognized that increases in BAT temperature are indicative of an upregulation of thermogenesis in BAT. Thus, BAT temperature changes may be used to assist in placement and operation of the DBS electrode to deliver DBS to an optimal location in a target region of the brain and to provide regulated closed-loop control to increase efficiency of DBS while reducing energy consumption of the pulse generator. For the treatment of obesity, the region of the brain targeted may comprise any suitable region which can be used to treat weight reduction. For example, the target region of the brain may comprise a central nervous system structure associated with metabolism such as the paraventricular nucleus of the hypothalamus, the anterior piriform cortex, or other modulatory brain regions (examples of which are described below with regard to FIG. 5).

In order to monitor BAT temperature for identification of an optimal location in a target region of the brain for DBS during electrode placement and to provide regulated closed-loop control during DBS treatment, the DBS system 100 may further include a BAT temperature sensor 110 coupled to the pulse generator 108 via an extension line 122. The extension line 122 may comprise an insulated wire that runs beneath the skin of the patient to the implanted pulse generator 108. The BAT temperature sensor 110 may be placed at any suitable location within the patient which is at or near a depot of BAT. For example, BAT temperature sensor 110 may be placed within a region of the upper chest or neck of the patient, e.g., on or near a supraclavicular area 126 of the patient.

During placement of the electrode into the target region 114 of the brain 102 of the patent, BAT temperature measurements may be used to identify an optimal location for electrode stimulation in the target region 114. For example, an increase in BAT temperature as measured by BAT temperature sensor 110 may provide a functional assessment to accurately target DBS to a location in the brain associated with metabolism. Such an approach may provide a direct measure of the effectiveness of the stimulation for acutely driving the effector tissues that are believed to contribute to the desired endpoint and therefore may increase electrode placement accuracy compared with purely anatomical localization approaches which rely on imaging assistance, such as MRI or CT. Further, approaches which rely on MER for electrode placement utilize specialized equipment and expertise, demand dedicated intraoperative time to perform the recordings, and in most cases mandate that procedures are performed on awake patients under local anesthesia. Thus, placement of the electrode based on BAT temperature measurements may be performed at reduced cost compared to approaches that rely on MER, and potentially can be performed on patients under general anesthesia.

In some examples, BAT temperature measurements, e.g., as measured by a BAT temperature sensor 110, may be used alone to guide electrode placement to an optimal location for DBS delivery within a target region of the brain. However, in other examples, BAT temperature sensor measurements may be used together with other guiding approaches such as MRI and/or CT to assist in electrode placement. For example, following the creation of a burr hole in the skull of the patient, an imaging assisted approach may be used together with a lead anchoring device for introducing a cannula into the burr hole directed to a target region of the brain. The electrode may then be introduced into the cannula and DBS delivery via the electrode may be initiated while monitoring BAT temperature to determine the proper placement and/or operating conditions of the electrode. The proper placement and/or operating conditions of the electrode may be identified by an increasing BAT temperature condition. For example, if an increasing BAT temperature condition does not occur while the electrode delivers DBS to a first location in a target region of the brain, then the position and/or operating conditions of the electrode may be adjusted until an increasing BAT temperature condition occurs during delivery of DBS to an adjusted location in the target region. Once the electrode is adjusted to deliver DBS to an optimal location identified by an increasing BAT temperature condition, then the electrode may be fixed or secured in place, e.g., via an electrode anchor 118. For example, the electrode anchor may comprise a burr hole ring and cap for secure anchoring of the electrode.

The BAT temperature measurements, e.g., as received by controller 128 from temperature sensor 110, may additionally be used to provide regulated closed-loop control to increase efficiency of DBS while reducing energy consumption of the implanted pulse generator. In particular, after the DBS electrode 106 is secured via the electrode anchor 118 for DBS delivery to an optimal location in a target region of the brain, during DBS treatment BAT temperature measurements may be provided as feedback to the pulse generator to control actuation and deactuation of DBS delivery to the target region in order to maintain a desired amount of active metabolism in the BAT. For example, DBS may be delivered to the target region of the brain via the electrode when the BAT temperature is less than a predetermined BAT temperature threshold and discontinued when the BAT temperature is greater than or substantially equal to the predetermined BAT temperature threshold.

Such an approach exploits a direct connection between BAT activation and brain stimulation to adjust delivery of DBS to the target region of the brain in real-time and thereby may preserve energy stored in the pulse generator, e.g., may extend the life of a battery within the pulse generator, while reducing occurrences of brain resistance to the therapy. In particular, previous approaches provide continuous stimulation without monitoring functional responses of the DBS treatment in real-time and therefore may waste energy and increase occurrences of resistance to the therapy. For example, in such previous approaches, constant DBS may lead to brain accommodation to the DBS such that effectiveness of the DBS is reduced.

Additionally, in some embodiments, core brain temperature measurements may be obtained from the DBS electrode 106, e.g., via a temperature sensor 130 integrated within the electrode 106, in order to monitor core temperature in the brain. The core temperature measurements in the brain may be used to adjust DBS delivery. For example, in response to core temperature measured at the electrode increasing above a core temperature threshold, delivery of DBS via the electrode may be discontinued until the core temperature falls below the core temperature threshold. In this way, core temperature may be monitored within the brain at the electrode to provide a fail-safe mechanism during DBS.

Figure 2:
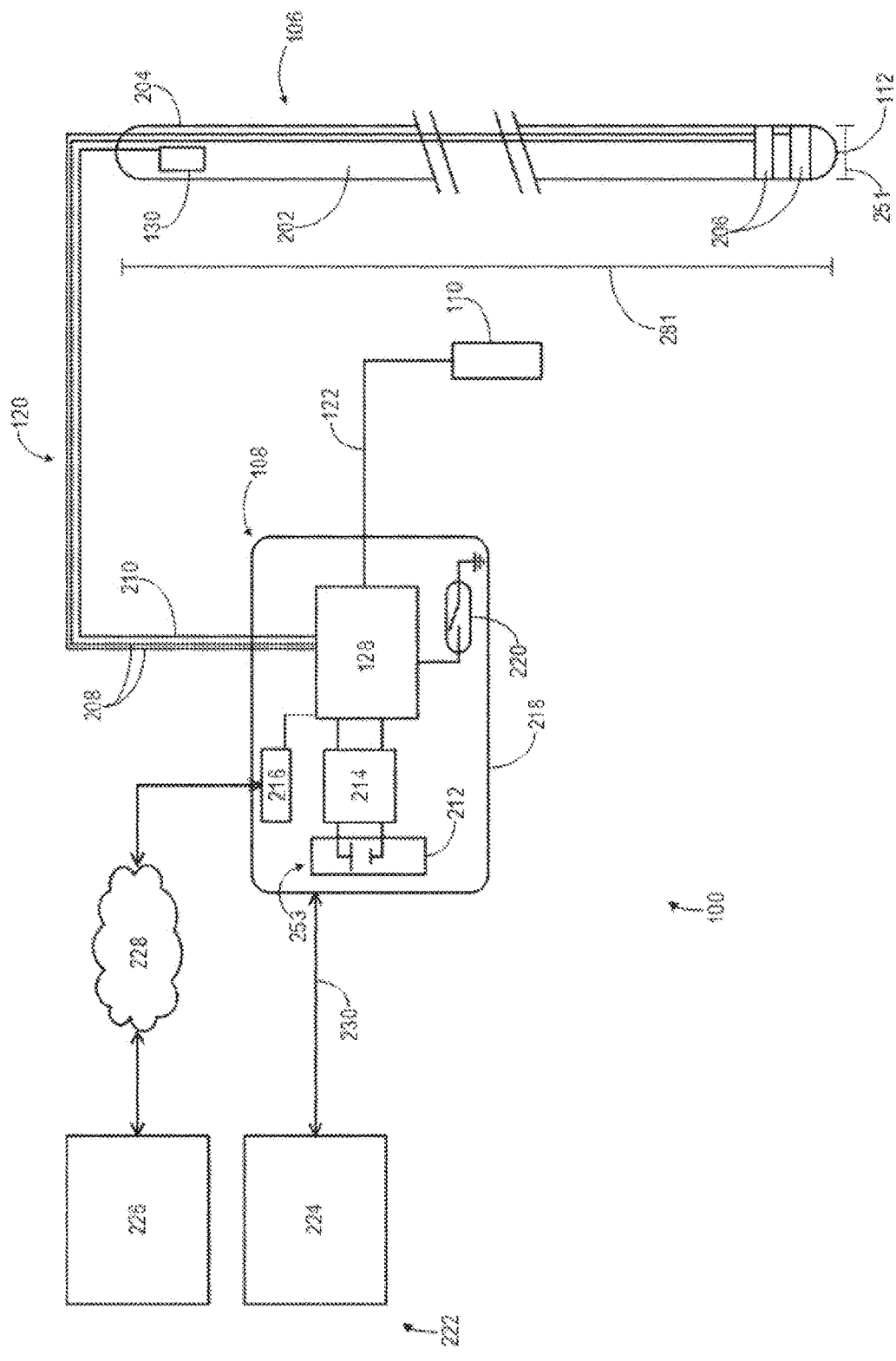
FIG. 2 shows a schematic diagram of an example deep brain stimulation system in accordance with the disclosure.

FIG. 2 shows a schematic diagram of an example DBS system 100. Numbered elements shown in FIG. 2 correspond to like-numbered elements shown in FIG. 1 described above. DBS system 100 may be used for the treatment of obesity, e.g., for body weight reduction, hypertension, or other indications which could benefit from DBS treatment such as diabetes.

DBS system 100 comprises an implantable pulse generator 108, an electrode 106 coupled to the pulse generator 108, and a BAT temperature sensor 110 coupled to the pulse generator 108. The implantable pulse generator 108 comprises an implantable housing 218 which may include various components such as a controller 128. Controller 128 may comprise microelectronic circuitry programmed to deliver controlled electrical pulses via the electrode to a precisely targeted area of the brain. The implantable housing may be composed of any material suitable for implantation in a patient, e.g., titanium.

The electrode comprises a cylindrically-shaped removable electrode stylet 202 with a soft, blunt tip 112 and may be composed of any suitable material, e.g., tungsten, and may have any suitable length 281 and diameter 251, e.g., the diameter of the electrode may be approximately 1.2 mm. The electrode 106 may be coupled to pulse generator 108 via an extension line 120. Extension line 120 may comprise wrapped or insulated wires, e.g., coiled wires, including electrode leads 208 which are coupled to electrode contacts 206, e.g., platinum iridium electrode contacts, at a distal end of the electrode adjacent to the tip 112 of the electrode. Though FIG. 2 shows two electrical contacts 206, it should be understood that any suitable number of contacts may be included on electrode 106, e.g., 4 or 6 contacts. In some embodiments as described in more detail below, an activation configuration of the electrical contacts on electrode 106 may be adjusted in order to change a location of DBS delivery in a target region of the brain without physically moving the electrode.

In some embodiments, the electrode 204 may include a temperature sensing component, e.g., temperature sensor 130. Temperature sensor 130 may be any suitable temperature sensor coupled to, mounted on, or integrated within electrode 106. In embodiments, temperature sensor 130 may comprise a thermistor coupled to an exterior surface or positioned within the electrode at any suitable location. For example, the thermistor may comprise a contact composed of a suitable thermistor material on the electrode such that when a small voltage is applied across the contact, the current that flows through the contact may be measured. For a given voltage applied across the contact, the current flow will change with the temperature of the thermistor material composing the contact and thus the current output may be calibrated and used to provide a temperature readout. Other example temperature sensors which may be integrated within or coupled to the electrode include thermocouples, resistance temperature detectors (RTDs), and non-contact temperature sensing components and technologies such as infrared (IR) temperature sensors and microwave radiometry. In some embodiments, temperature sensor 130 may be positioned adjacent to an end of the electrode opposing the tip 112. As another example, temperature sensor 130 may comprise a flexible sheet or thin film integrated with or adhered to an exterior surface of electrode 106. In some embodiments, the temperature sensing component may comprise the electrode contacts 206. For example, measurements received by controller 128 from the contacts 206 may be processed in any suitable manner to extract temperature data.

By including a temperature sensing component at the electrode 106, when the electrode is implanted in the brain of the patient, the temperature component may be used to measure core temperature within the brain during electrode placement and/or during DBS treatment. The extension line 120 may additionally include a temperature input and feedback line 210 which is in communication with controller 128 for sending and receiving signals to monitor core temperature in the brain via the electrode.

The BAT temperature sensor 110 in DBS system 100 may be implanted in a region of BAT in a patient, such as on or near a supraclavicular area 126 of the patient. In some embodiments, BAT temperature sensor 110 may be coupled to the pulse generator 108 via an extension line 122. Extension line 122 may be composed of any suitable material which can be implanted subcutaneously in a patient and may comprise wrapped or insulated wires including temperature input and feedback lines. BAT temperature sensor 110 may comprise any suitable temperature sensing component, e.g., a thermistor, thermocouple, RTD, non-contact temperature sensor, etc. In some embodiments, BAT temperature sensor 110 may be coupled to, included in, or integrated with pulse generator 108. For example, temperature sensor 110 may coupled onto or within housing 218 of pulse generator 108 and the pulse generator may be implanted at or near a region of BAT in the patient so that BAT temperature may be monitored by the temperature sensor at the pulse generator.

The pulse generator 108 may include any suitable energy source 253 within the housing 218. For example, the pulse generator may include a battery 212. Battery 212 may comprise any suitable rechargeable or non-rechargeable battery. In some examples, pulse generator 108 may include voltage regulator 214 coupled to the battery 212 and the controller 128 to regulate voltage supplied by the battery to the controller. Pulse generator 108 may additionally include a reed switch 220 and other components not shown in FIG. 2, e.g., fail-safe circuitry, shielding components configured to shield the pulse generator from electromagnetic fluctuations, etc. Reed switch 220 may be coupled to controller 128 and may be activated via a magnetic field to control operating conditions of the pulse generator, e.g., to deactivate the pulse generator or to adjust various operating parameters of the pulse generator.

The controller 128 may comprise any suitable computing component, such as the computing device 700 described below with regard to FIG. 7. Controller 128 may include a logic subsystem and a data-holding subsystem, where the logic subsystem may include one or more physical devices with circuitry programmed to execute one or more machine-readable instructions to perform various processing routines, examples of which are described below. For example, controller 128 may be configured to send, receive, and process signals from electrode 106, receive and process signals from temperatures sensors 110 and 130, and to send, receive, and process signals from various external devices or systems 222.

Pulse generator 108 may also include a communication subsystem 216 configured to send and receive data over a network 228 to external devices or systems such as external system 226 and/or may be configured to send and receive data via a connection 230 to external systems such as external system 224. External systems 222 may comprise various devices and/or systems such as computing devices, display devices, battery recharging devices, mobile devices, monitoring systems, sensors, etc. Network 228 may include any suitable network, e.g., a wireless telephone network, a wireless local area network, a wired local area network, a wireless wide area network, a wired wide area network, the Internet, etc. Connection 230 may comprise any suitable communication channel, e.g., a wireless connection such as a near field communication (NFC) channel, a radio frequency (RF) channel, Bluetooth, etc., or a cabled connection coupling one or more external devices or systems to pulse generator 108.

In embodiments, external systems 222 may include activity monitoring systems which track and process various activities and/or physiological parameters of a patient within which the pulse generator 108 is implanted. Such activity monitoring systems may include a variety of sensors and components, such as temperature sensors, blood pressure sensors, heart-rate sensors, accelerometers, metabolic activity sensors, global positioning system (GPS) components, memory components, and processors comprising circuitry which are programmed to collect, process, store, and output data to the pulse generator 108. For example, an activity monitoring system may be configured to track and quantify movements of the patient, e.g., number of steps taken and distance travelled, and to track and quantify sleep patterns of the patient. Such data may be sent to controller 128 in pulse generator 108 so that DBS may be adjusted accordingly as described below. In some embodiments, one or more activity monitoring systems may be included within pulse generator 108 to track activity levels of the patient for real-time DBS adjustment.

As another example, external systems 222 may include a glucose monitoring system or a blood glucose metering system which is configured to monitor glycemic changes, and/or blood levels of glucose, lipid and insulin, for example. Such a glucose monitoring system may include a variety of sensors and components, such as a glucose sensor which can be inserted under the skin of the patient to monitor glucose levels in tissue fluid. As another example, a glucose monitoring system may be configured to receive input from a fingerstick performed on the patient to track and calibrate glucose readings. The glucose monitoring system may be configured to process measurements and/or inputs to identify glucose patterns and to output data to the pulse generator 108. In some embodiments, a glucose monitoring system may be included within pulse generator 108 to monitor glycemic changes and blood levels of glucose, lipid and/or insulin for DBS adjustment.

Via communication subsystem 216, Pulse generator 108 may be configured to output data, e.g., temperature measurements from temperature sensors 110 and/or 130, for display on a display device or for storage on a memory component of an external computing device. Pulse generator 108 may also be configured to output various indications and/or notifications to one or more external devices of operational conditions of the pulse generator. Additionally, pulse generator 108 may be configured to receive input signals and/or data from one or more external devices or systems for adjusting operating parameters, recharging the battery, initiating/deactivating various operational modes, programming, etc.

Figure 3:
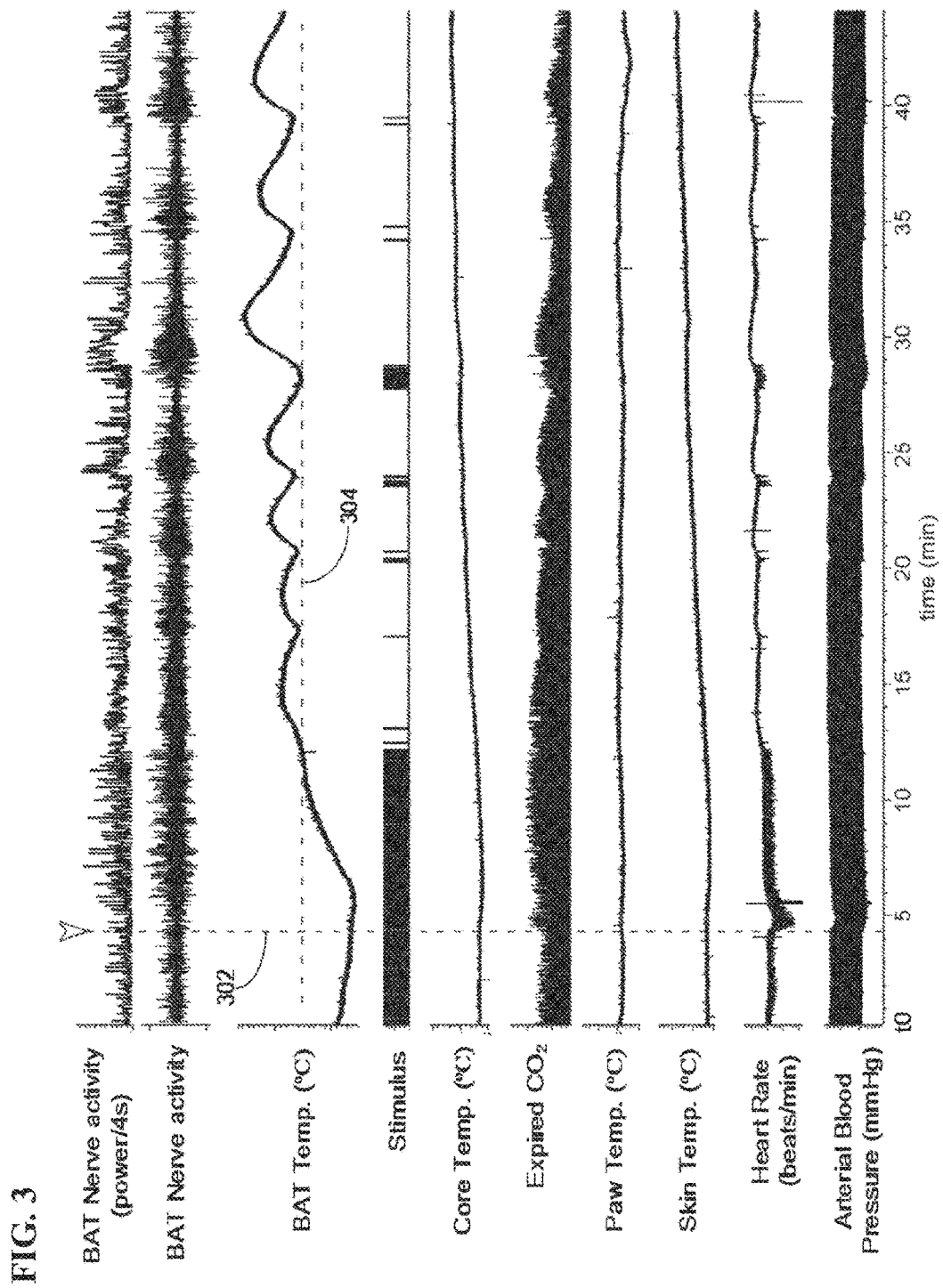
FIG. 3 shows example data illustrating an example method for deep brain electrode placement and stimulation in accordance with the disclosure.
Figure 4:
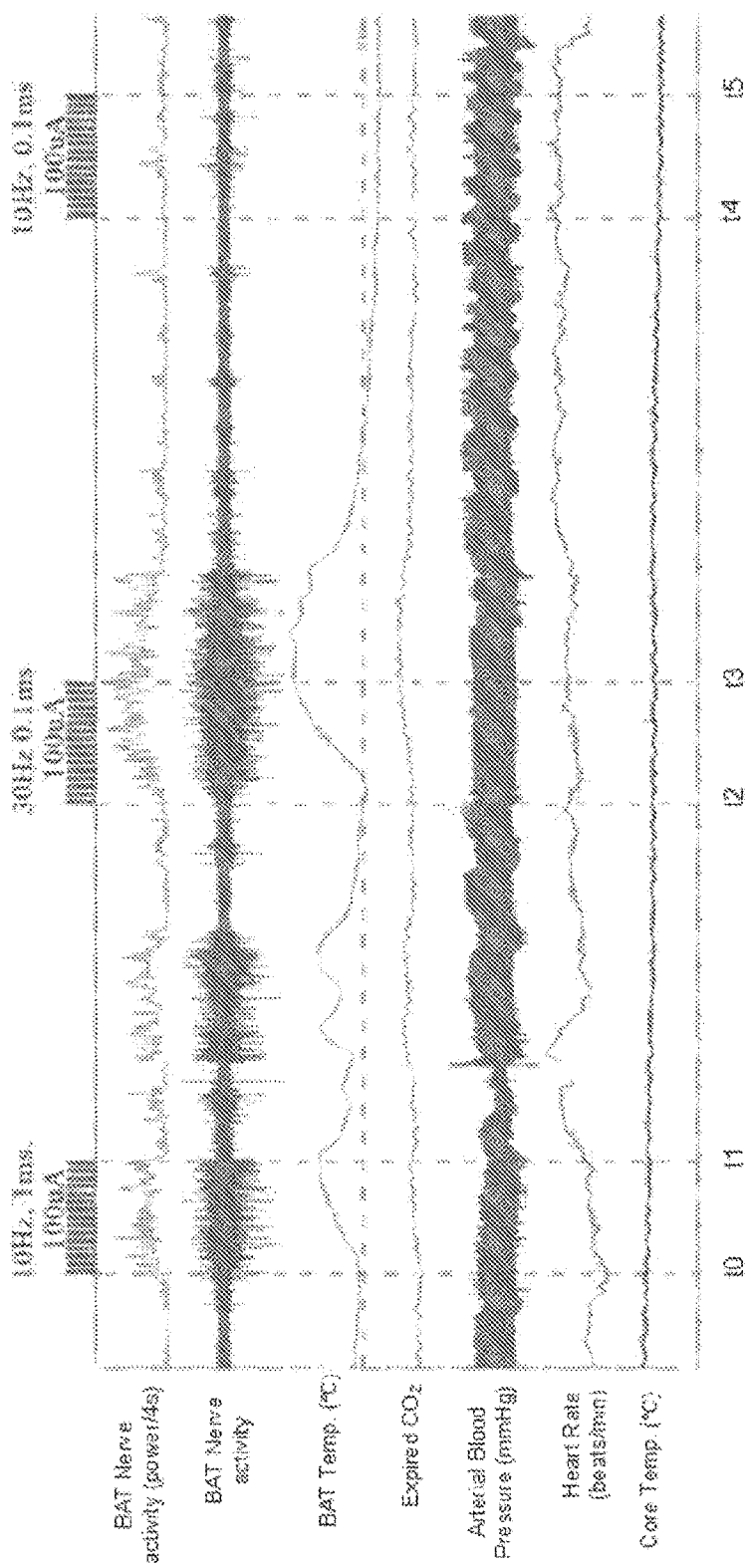
FIG. 4 shows example data for different deep brain stimulation parameters.

FIG. 3 shows example data illustrating an example method, such as method 600 described below, for deep brain electrode placement and stimulation. FIG. 4 shows example data for different DBS parameters which may be used in selecting DBS stimulation parameters. The data shown in FIGS. 3 and 4 were obtained from DBS experiments performed by electrical stimulation of the paraventricular nucleus of the hypothalamus in the rat. The methods used in these experiments are described in the following.

Male Wistar rats (Charles River, Indianapolis, Ind.) weighing 680 g and 429 g were kept on a 12:12 hour light dark cycle and given ad libitum access to standard rat chow and water in a colony room maintained at 22-23.degree. C. Rats were anesthetized with isoflurane (2-3% in oxygen), instrumented with femoral arterial and venous catheters and transitioned to urethane and chloralose anesthesia (750 mg/kg and 60 mg/kg iv, respectively) over a ten minute period. All physiological variables were digitized (Micro 1401 MKII; Cambridge Electronic Design (CED), Cambridge, UK) and recorded onto a computer hard drive for subsequent analysis (Spike 2, CED). Arterial blood pressure was recorded from the arterial catheter attached to a pressure transducer and heart rate (HR) was derived from the arterial pressure signal. The trachea was cannulated, and the animal was ventilated (tidal volume: ~1 ml per 100 g body weight, ~60 cycles per minute) with 100% oxygen (FIG. 4) or was allowed to freely breathe oxygen enriched room air (FIG. 3). A capnometer (model 2200; Dynatech Electro-optics, Saline, Mich., USA) was used to measure end-expiratory $CO_2$ via a needle probe inserted into the trachea tube. Adequacy of anesthesia was verified by absence of a withdrawal reflex or pressor response to foot pinch as well as by absence of a corneal reflex. Colonic (core) temperature (Tcore) was monitored using a copper-constantan thermocouple inserted 6 cm into the rectum and was maintained between 35-38.degree. C. with a water-perfused heating/cooling blanket and a heat lamp. The trunk skin was shaved and copper-constantan thermocouples were taped to the hindquarter skin to monitor skin temperature (Tskin) beneath the heating/cooling blanket and to the forepaw to monitor paw skin temperature (Tpaw). The temperature of BAT (TBAT) was monitored using a thermocouple meter (TC-1000, Sable Systems International, Las Vegas, Nev., USA) with a Type T needle style microprobe thermocouple (Physitemp, Clifton, N.J., USA) inserted into the intact, left interscapular BAT fat pad. Postganglionic BAT sympathetic never activity (SNA) was recorded under mineral oil with a bipolar hook electrode from the central cut end of a small diameter nerve bundle isolated from the ventral surface of the right interscapular fat pad after dividing it along the midline and reflecting it laterally. Nerve activity was filtered (1-300 Hz) and amplified (10,000.times.) with a Cyberamp 380 (Axon Instruments, Union City, Calif.). Spike 2 software (CED) was used to obtain a continuous measure (4 s bins) of BAT SNA amplitude by calculating the root mean square (rms) amplitude of the BAT SNA (square root of the total power in the 0.1 to 20 Hz band) from the autospectra of sequential 4-s segments of BAT SNA. Animals were placed in a stereotaxic frame and stimulating microelectrodes were placed into the hypothalamus.

FIG. 3 shows time plots of data collected for integrated BAT sympathetic nerve activity (power/4 s), actual BAT sympathetic nerve activity (.mu.V), BAT temperature (.degree. C.), DBS stimulus activation (V), core temperature (.degree. C.), expired $CO_2$(%), paw temperature (.degree. C.), skin temperature (.degree. C.), heart rate (beats/min), and arterial blood pressure (mmHg). The data shown in FIG. 3 demonstrates the ability to activate thermogenesis in rat BAT while causing decreases in arterial pressure by electrical stimulation of the paraventricular nucleus of the hypothalamus in the rat. Thermogenesis is an energy consuming process that is the basis for the potential of DBS to cause weight loss.

At time t0 in FIG. 3, the electrode was positioned to deliver DBS to a first location near (just outside) the paraventricular nucleus of the hypothalamus in the rat and DBS was delivered as indicated by the stimulus plot. Delivering DBS comprised delivering, via the electrode, electrical impulses to the target region of the brain. The electrical impulses had a pre-selected frequency, amplitude, and pulse duration and were successively delivered for a pre-selected on-duration and discontinued for a pre-selected off-duration. In this example, the DBS stimuli was delivered at a 50 Hz frequency, 100 .mu.A amplitude, 100 .mu.s pulse duration, and the on-duration and off-duration were both 5 seconds so that, when activated, electrical impulses were delivered for 5 seconds, discontinued for 5 seconds, again delivered for 5 seconds, and so forth.

As indicated by the BAT temperature measurements shown in FIG. 3 immediately following time t0, the first location of electrode stimulation was not producing an increase in the BAT temperature. In particular, between times t0 and the time point indicated by cursor 302, there was a non-increasing BAT temperature condition where the BAT temperature decreased and was less than a predetermined BAT temperature threshold 304. In this example, the predetermined BAT temperature threshold 304 was approximately 34.5.degree. C. However, any suitable BAT temperature threshold may be selected based on an amount of desired thermogenesis activation in the BAT.

At the time indicated by cursor 302 in FIG. 3, the electrode was adjusted to deliver DBS to an adjusted location. In particular, in this example the electrode was moved approximately 0.5 mm deeper into the paraventricular nucleus of the hypothalamus in the rat. Following this adjustment of the electrode to deliver DBS to the adjusted location in the paraventricular nucleus, an increasing BAT temperature condition was observed as shown in the BAT temperature plot in FIG. 3. In particular, following the electrode adjustment, the BAT temperature increased to the predetermined BAT temperature threshold 304. This increasing BAT temperature condition indicated that an optimal location of electrode stimulation in the paraventricular nucleus of the hypothalamus had been found and thus that the electrode may be secured in place at that location so that DBS may be effectively performed.

Whenever the BAT temperature exceeded the BAT temperature threshold 304, delivery of DBS was discontinued as shown in FIG. 3 and only reactivated when the BAT temperature decreased below the BAT temperature threshold 304 so as to provide regulated closed-loop control to increase efficiency of DBS while reducing energy consumption of the pulse generator.

Though the DBS stimuli were delivered at a 50 Hz frequency, a 100 .mu.A amplitude, and a 100 .mu.s pulse duration with a 5 second on-duration and a 5 second off-duration in this example, various other DBS parameters may be used. Example ranges for stimulus parameters are frequencies in the approximate range of 5 Hz-200 Hz, amplitudes in the approximate range of 10 .mu.A-1 mA, and pulse durations in the approximate range of 10-250 .mu.s. It should be understood that these example ranges are given by way of example and are not intended to be limiting. In some embodiments, the particular stimulation parameters used during DBS treatment may be selected based on predetermined data which identifies stimulation parameters that lead to maximal increases in BAT temperature.

For example, FIG. 4 shows example data for different DBS parameters which may be used in selecting DBS stimulation parameters. In particular, FIG. 4 shows time plots of data collected for integrated BAT sympathetic nerve activity (power/4 s), actual BAT sympathetic nerve activity (.mu.V), BAT temperature (.degree. C.), expired $CO_2$ (%), arterial blood pressure (mmHg), heart rate (beats/min), and core temperature (.degree. C.) measured for different DBS stimuli parameters. For example, between times t0 and t1 in FIG. 4, the stimuli parameters were 10 Hz frequency, 1 ms pulse duration, and 100 .mu.A amplitude; between times t2 and t3 the stimuli parameters were 30 Hz frequency, 0.1 ms pulse duration, and 100 .mu.A amplitude; and between times t4 and t5 the stimuli parameters were 10 Hz frequency, 0.1 ms pulse duration, and 100 .mu.A amplitude. Such data may be used to select optimal stimulation parameters for maximal BAT temperature increases during DBS. For example, the data shown in FIG. 4 indicated that the DBS stimuli with parameters 30 Hz, 0.1 ms, and 100 .mu.A led to the greatest rate of increase in BAT temperature.

Figure 5:
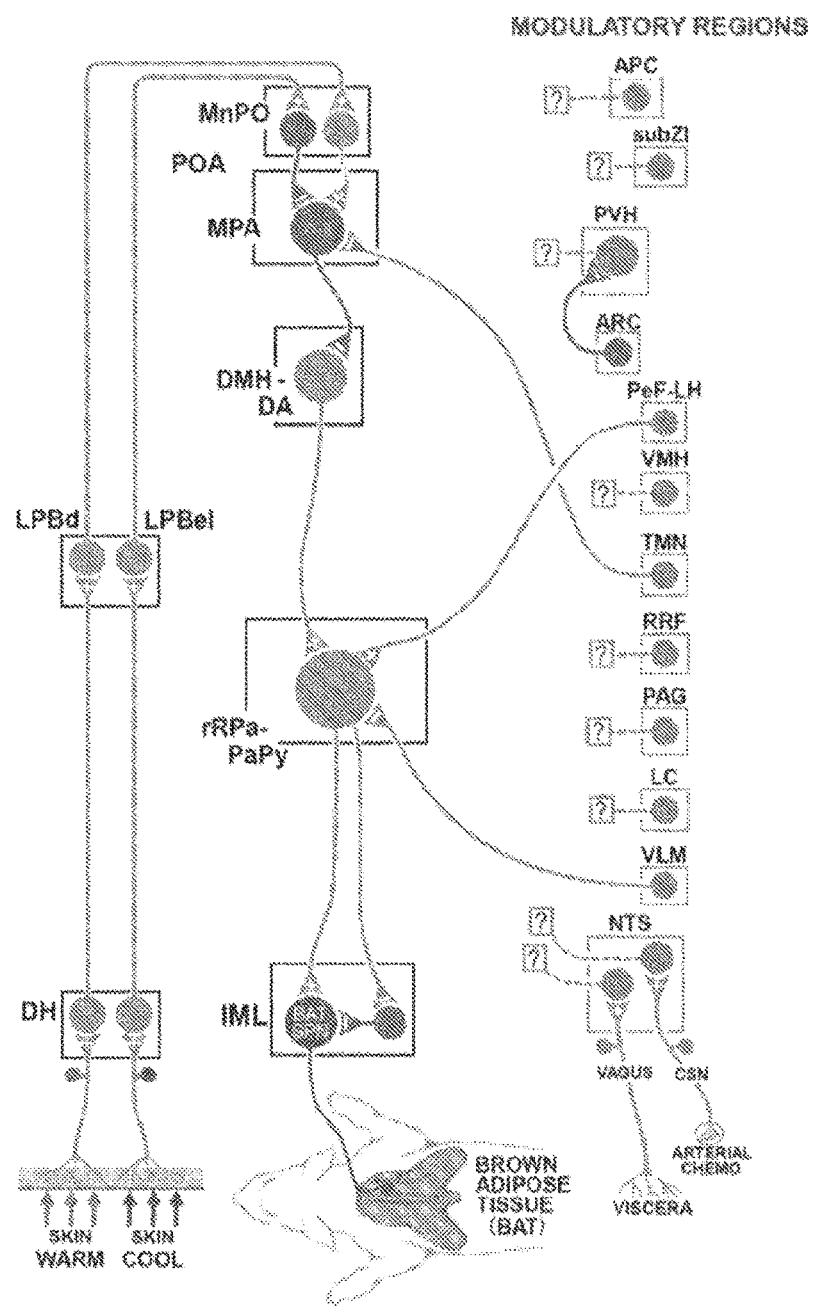
FIG. 5 shows an example model for the neuroanatomical organization of the core thermoregulatory network and other central nervous system (CNS) sites controlling and modulating brown adipose tissue thermogenesis.

FIG. 5 shows an example model for the neuroanatomical organization of the core thermoregulatory network and other central nervous system (CNS) sites controlling and modulating BAT thermogenesis. The model shown in FIG. 5 and described below provides example non-limiting modulatory brain regions which may be selected as target regions for DBS delivery as described herein. For example, as illustrated in FIG. 5, the target regions selected for DBS may comprise one or more of the anterior piriform cortex (APC), the arcuate nucleus (ARC), the locus coeruleus (LC), the periaqueductal gray (PAG), the paraventricular hypothalamus (PVH), the retrorubral fields (RRF), the sub zona incerta (subZI), and the ventromedial hypothalamus (VMH). As illustrated in FIG. 5, cool and warm cutaneous thermal sensory receptors transmit signals to respective primary sensory neurons in the dorsal root ganglia which relay this thermal information to second-order thermal sensory neurons in the dorsal horn (DH). Cool sensory DH neurons glutamatergically activate third-order sensory neurons in the external lateral subnucleus of the lateral parabrachial nucleus (LPBel), while warm sensory DH neurons project to third-order sensory neurons in the dorsal subnucleus of the lateral parabrachial nucleus (LPBd). Thermosensory signals for thermoregulatory responses are transmitted from the LPB to the preoptic area (POA) where GABAergic interneurons in the median preoptic (MnPO) subnucleus are activated by glutamatergic inputs from cool-activated neurons in LPBel and inhibit a BAT-regulating population of warm-sensitive (W-S) neurons in the medial preoptic area (MPA). In contrast, glutamatergic interneurons in the MnPO, postulated to be excited by glutamatergic inputs from warm-activated neurons in LPBd, excite W-S neurons in MPA. Preoptic W-S neurons providing thermoregulatory control of BAT thermogenesis inhibit BAT sympathoexcitatory neurons in the dorsomedial hypothalamus and dorsal hypothalamic area (DMH/DA) which, when disinhibited during skin cooling, excite BAT sympathetic premotor neurons in the rostral ventromedial medulla, including the rostral raphe pallidus (rRPa) and parapyramidal area (PaPy), that project to BAT sympathetic preganglionic neurons (SPN) in the spinal intermediolateral nucleus (IML). Some BAT premotor neurons can release glutamate to excite BAT sympathetic preganglionic neurons and increase BAT sympathetic nerve activity, while others can release serotonin to interact with 5-HT1A receptors, potentially on inhibitory interneurons in the IML, to increase the BAT sympathetic outflow. Modulatory regions represent areas of the CNS that are not within the core thermoregulatory pathway, but from which chemical or electrical manipulation of the activity of local neurons produced effects on BAT activity. Dotted lines to question marks indicate that the pathway mediating the effect on BAT activity is currently unknown. Orexinergic neurons in the perifornical lateral hypothalamus (PeF-LH) project to the rRPa to increase the excitability of BAT sympathetic premotor neurons. Histaminergic neurons in the tuberomammillary nucleus (TMN) project to the POA to increase BAT activity by influencing the discharge of neurons in the core thermoregulatory pathway. Activation of neurons in the ventrolateral medulla (VLM) produces an inhibition of BAT thermogenesis, at least in part by noradrenergic (NE) activation of a2 receptors on rRPa neurons. Neurons in the nucleus of the solitary tract (NTS) mediate the effects of afferents in the vagus and carotid sinus (CSN) and aortic depressor nerves.

Figure 6:
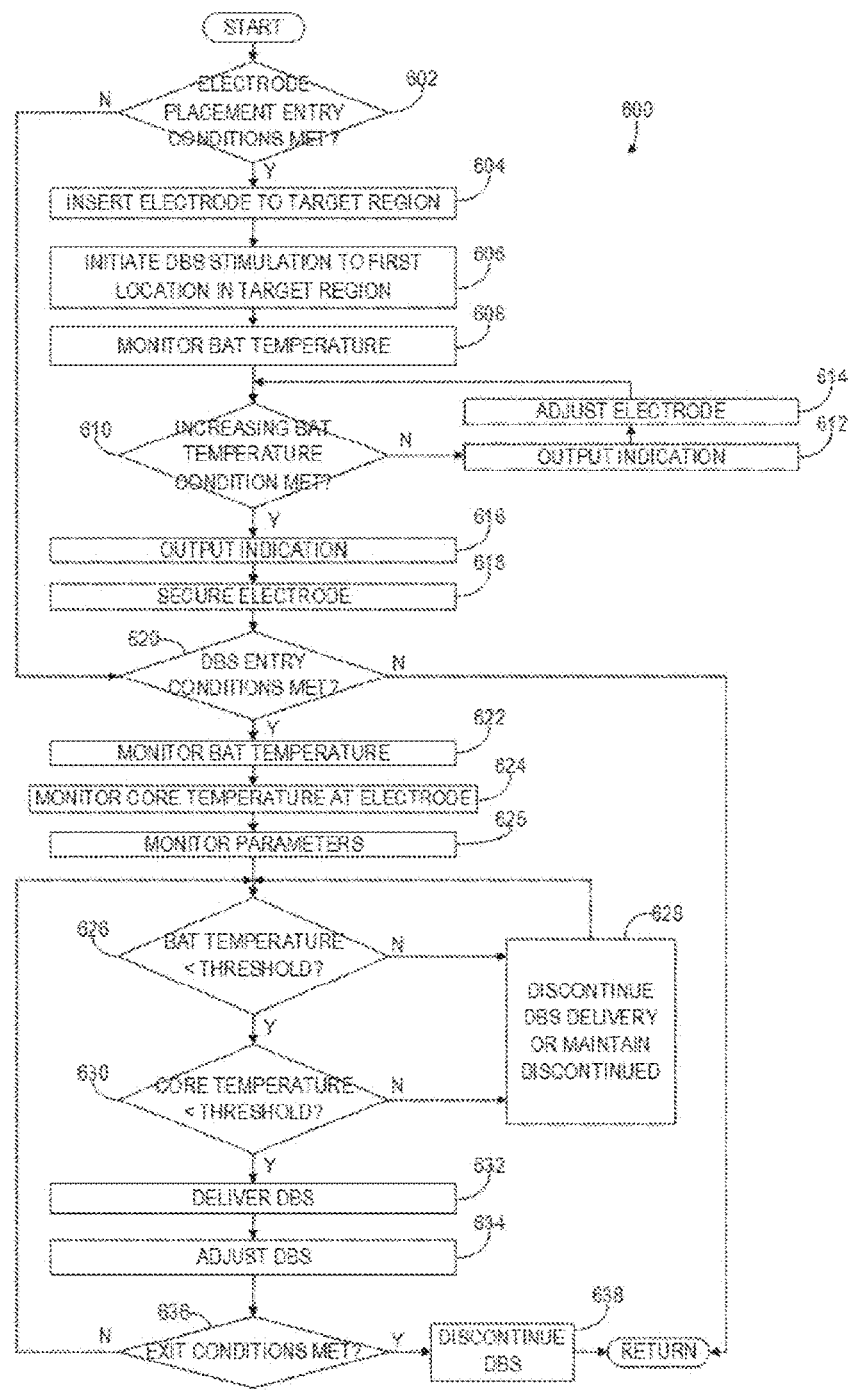
FIG. 6 shows an example method for deep brain electrode placement and stimulation in accordance with the disclosure.

FIG. 6 shows an example method 600 for deep brain electrode placement and stimulation based on BAT temperature measurements. Method 600 may be performed by DBS system 100 to identify optimal positioning of electrode stimulation and to regulate DBS for the treatment of various conditions such as obesity and diabetes. In particular, controller 128 in pulse generator 108 may be configured to automatically perform one or more steps of method 600. It should be understood that the various acts illustrated in method 600 may be performed in the sequence illustrated, in other sequences, in parallel, or in some cases omitted.

At 602, method 600 includes determining if electrode placement entry conditions are met. Examples of electrode placement entry conditions may include an amount of energy stored in the battery 212 greater than a threshold, connection and coupling of the various components of the DBS system, a power-on event in the DBS system, DBS stimulation parameter input, etc. Electrode placement entry conditions may follow various surgical routines performed prior to electrode placement in the brain of a patient such as the creation of a burr hole in the skull of the patient and an introduction of a cannula into the burr hole directed to a target region of the brain. If electrode placement entry conditions are not met at 602, then method 600 may proceed to 620 to determine if DBS entry conditions are met as described below. However, if electrode placement entry conditions are met at 602, then method 600 proceeds to 604.

At 604, method 600 includes inserting a DBS electrode to the target region of the brain of the patient to deliver DBS to a first location in the target region. The target region of the brain may comprise a central nervous system structure associated with metabolism. For example, the target region of the brain may comprise the paraventricular nucleus of the hypothalamus, the anterior piriform cortex, or other modulatory brain regions (examples of which are described above with regard to FIG. 5).

At 606, method 600 includes initiating DBS stimulation. For example, following an initial insertion of the electrode to the target region to deliver DBS to a first location in the target region of a brain, DBS delivery to the target region may be initiated in any suitable way. As an example, a clinician may provide input to the pulse generator via an external device or via an input in or on the pulse generator to activate DBS delivery to the target region of the brain via the electrode. As one example, delivering DBS may comprise delivering, via the electrode, electrical impulses to the target region of the brain. The electrical impulses may have a predetermined frequency, predetermined amplitude, and predetermined pulse duration and may be successively delivered for an on-duration and discontinued for an off-duration. As another example, if the electrode is a thermode, then delivering DBS may comprise cooling the target region via the thermode, e.g., decreasing the temperature of the target region of the brain via the thermode.

At 608, method 600 includes monitoring BAT temperature in the patient. For example, BAT temperature sensor 110 may be used to monitoring a BAT temperature on or near a supraclavicular area of the patient or at any other BAT location in the patient. Controller 128 in pulse generator 108 may be configured to receive and process the BAT temperature measurements from BAT temperature sensor 110. In some embodiments, monitoring BAT temperature may additionally include adjusting the BAT temperature based on an ambient temperature. In particular, DBS system 100 may include an ambient temperature sensor and controller 128 may be configured to receive ambient temperature measurements from the ambient temperature sensor and adjust the BAT temperature measurements based on the ambient temperature measurements. For example, in response to an increasing ambient temperature, the BAT temperature measurements may be decreased proportionally. Additionally, controller 128 may be configured to output the BAT temperature measurements to an external device for storage thereon or to a display device to assist in guiding a clinician in placing the electrode to deliver DBS to an optimal location in the target region of the brain.

At 610, method 600 includes determining if an increasing BAT temperature condition is met. For example, the increasing BAT temperature condition may comprise an increase in BAT temperature for a predetermined duration. As another example, the increasing BAT temperature condition may comprise an increase in BAT temperature to a predetermined BAT temperature threshold. In some examples, controller 128 in pulse generator 108 may be configured to identify an increasing BAT temperature condition based on measurements received from the temperature sensor 110. In response to an identification of an increasing BAT temperature condition, the controller may output an indication, e.g., to a display device and/or an audio device, to notify a clinician whether or not an increasing BAT temperature condition occurs.

If an increasing BAT temperature condition is not met at 610, then a non-increasing BAT temperature condition may have occurred. For example, a non-increasing BAT temperature condition may comprise a decrease in BAT temperature for a predetermined duration. Method 600 may then proceed to 612. At 612, method 600 may include outputting an indication of the non-increasing BAT temperature condition. For example, controller 128 may be configured to output an indication to a display device or an audio device to notify the clinician to adjust the electrode until an increasing BAT temperature condition occurs. Any suitable indication of the non-increasing BAT temperature condition may be output by the DBS system. For example, BAT temperature sensor measurements may be continuously output to a display device so that the clinician can identify a non-increasing BAT temperature condition based on the displayed BAT temperature measurements and adjust the electrode accordingly. As another example, visual and/or audio indications may be provided to the clinician via a display device or via one or more speakers to indicate the non-increasing BAT temperature condition in order to instruct the clinician to adjust the electrode to deliver DBS to an adjusted location in the target region of the brain.

At 614, method 600 may include adjusting the electrode for delivery of DBS to an adjusted location in the target region of the brain. As one example, a physical position of the electrode may be adjusted so that DBS is delivered to an adjusted location in the target region of the brain. As another example, operational parameters of the electrode may be adjusted in response to the non-increasing brown adipose tissue temperature condition so that stimulation is delivered to an adjusted location within the target region without physically moving the electrode. Any suitable operational parameters of the electrode may be adjusted to move the location of DBS delivery within the target region. For example, an activation configuration of electrode contacts of the electrode may be adjusted to move the location of DBS delivery in the target region without moving the electrode itself. As an example, if an electrode has more than two electrode contacts, e.g., 4 or 6 contacts, then a depth of stimulation may be adjusted by changing which contacts of the electrode are actively used to deliver DBS. For example, if four contacts are equally spaced by 0.5 mm on the electrode with a first contact adjacent to the tip of the electrode, a second contact separated from the first contact by 0.5 mm in a direction away from the tip, a third contact separated from the second contact by 0.5 mm in a direction away from the tip, and a fourth contact separated from the third contact by 0.5 mm in a direction away from the tip, then adjustment of the electrode to utilize the first contact as the negative pole and the second contact as the positive pole would achieve a depth of stimulation approximately 0.5 mm deeper than operating conditions of the electrode where the third contact is used as the negative pole and the fourth contact is used as a positive pole.

After the electrode is adjusted to deliver DBS to an adjusted location in the target region, method 600 may return to 610 to determine if an increasing BAT temperature condition occurs during DBS delivery to the adjusted location. For example, a clinician may adjust the physical position of the electrode or adjust operational parameters of the electrode contacts and then wait for a predetermined wait duration, e.g., approximately 60 seconds, to see if an increasing BAT temperature condition occurs while the electrode delivers DBS to the adjusted location. In some embodiments, the controller 128 may be configured to output an indication that this predetermined wait duration has elapsed, e.g., via an output to a display device or an audio device. If an increasing BAT temperature condition does not occur while the electrode delivers DBS to the adjusted location then the electrode may again be adjusted until an increasing BAT temperature condition occurs.

Once an increasing BAT temperature condition is met at 610, method 600 proceeds to 616. At 616, method 600 may include outputting an indication of the increasing BAT temperature condition. For example, controller 128 may be configured to output an indication to a display device or an audio device to notify the clinician that an optimal location of DBS delivery via the electrode has been achieved and to instruct the clinician to secure the electrode in place. At 618, method 600 includes securing the electrode for delivery of DBS to the optimal location identified by the increasing BAT temperature condition. For example, a clinician may secure the electrode via electrode anchor 118.

At 620, method 600 includes determining if DBS entry conditions are met. DBS entry conditions may occur after the electrode is secured to deliver DBS to the optimal location identified by the increasing BAT temperature condition. DBS entry conditions may additionally follow surgical procedures where components of the DBS system are implanted in the patient. For example, during placement of the electrode, the pulse generator may remain external to the patient whereas following securing the electrode for DBS delivery to the optimal location, the pulse generator and the various extensions may be surgically implanted in the patient before DBS treatment is initiated. However, in other examples, DBS treatment may be initiated immediately following placement of the electrode for DBS delivery to the optimal location. DBS entry conditions may additionally include receiving an input to initiate DBS. For example, a clinician may provide input to the pulse generator to program the pulse generator to deliver electrical impulses with a predetermined frequency, predetermined amplitude, and predetermined pulse duration at predetermined intervals. Further, a predetermined BAT temperature threshold may be input into the pulse generator so that DBS may be successively delivered for an on-duration and discontinued for an off-duration based on the predetermined BAT temperature threshold.

If DBS entry conditions are met at 620, method 600 proceeds to 622. At 622, method 600 includes monitoring BAT temperature. For example, BAT temperature sensor 110 may be used to monitor a BAT temperature on or near a supraclavicular area of the patient or at any other location in the patient with BAT. In some embodiments, monitoring BAT temperature may additionally include adjusting the BAT temperature based on ambient temperature measurements received from an ambient temperature sensor. Controller 128 in pulse generator 108 may be configured to receive and process the BAT temperature measurements from BAT temperature sensor 110. Additionally, controller 128 may be configured to store BAT temperature measurements in a storage medium in pulse generator 108. The BAT temperature measurements may be used to provide regulated closed-loop control to increase efficiency of DBS while reducing energy consumption of the implanted pulse generator. For example, after a DBS electrode is secured for DBS delivery to an optimal location in a target region of the brain of a patient, BAT temperature measurements may be provided as feedback to the pulse generator to control when DBS is delivered and when DBS is discontinued in order to maintain a desired amount of active metabolism in the BAT. For example, DBS may be delivered to the target region of the brain via the electrode when the BAT temperature is less than a predetermined BAT temperature threshold and discontinued when the BAT temperature is greater than or substantially equal to the predetermined BAT temperature threshold.

At 624, method 600 may include monitoring core temperature at the electrode. For example, a temperature sensing component, such as temperature sensor 130, at the electrode may be used to monitor core temperature in the brain following an initiation of DBS treatment. Controller 128 may be configured to receive core temperature measurements from the temperature sensing component of the electrode and, in some examples, store the core temperature measurements in a storage medium in the pulse generator. The core temperature measurements may be used to provide a fail-safe mechanism during DBS. For example, in response to core temperature measured at the electrode increasing above a core temperature threshold, delivery of DBS via the electrode may be discontinued until the core temperature falls below the core temperature threshold.

At 625, method 600 may include monitoring various other parameters. For example, DBS system 100 may include various sensors or may be coupled to or in communication with various monitoring systems, e.g., an activity monitoring system and/or a glucose monitoring system, to track various parameters such as blood pressure, heart rate, skin temperature, expired CO.sub.2, activity, glycemic changes, blood levels of glucose, lipid, and/or insulin, etc. Such parameters may be continuously monitored in real-time and received by controller 128 so that the controller may adjust DBS in real-time based on these parameters.

At 626, method 600 includes determining if BAT temperature is less than the predetermined BAT temperature threshold. If BAT temperature is not less than the predetermined BAT temperature threshold at 626, e.g., if BAT temperature is greater than or substantially equal to the threshold, then method 600 proceeds to 628. At 628, method 600 includes discontinuing or deactivating DBS delivery or maintaining the delivery of DBS deactivated or discontinued. Method 600 then returns to 626 to monitor the BAT temperature.

If BAT temperature is less than the predetermined BAT temperature threshold at 626, then method 600 proceeds to 630. At 630, method 600 may include determining if core temperature measured at the electrode is less than a core temperature threshold. If core temperature is not less than the core threshold at 630, e.g., if core temperature is greater than or substantially equal to the threshold, then method 600 proceeds to 628 to discontinue or deactivate DBS delivery or maintain the delivery of DBS deactivated or discontinued. In this way, the core temperature measurements may provide a fail-safe mechanism to deactivate DBS if core temperatures in the brain become too high during DBS. Method 600 then returns to 626 to monitor the BAT temperature.

If core temperature measured at the electrode is less than the core temperature threshold at 630 then method 600 proceeds to 632. At 632, method 600 includes delivering DBS when the BAT temperature is less than the BAT temperature threshold and the core temperature is less than the core temperature threshold. Delivering DBS may comprise delivering, via the electrode, electrical impulses to the target region of the brain. The electrical impulses have a predetermined frequency, predetermined amplitude, and predetermined pulse duration and may be successively delivered for an on-duration and discontinued for an off-duration. In some embodiments, the electrode may be a thermode and delivering DBS to the target region may comprise cooling the target region via the thermode.

At 634, method 600 may include adjusting DBS. In particular, the DBS may be adjusted based on one or more parameters monitored in real-time as described in steps 622, 624, and 625 above. For example, one or more of the frequency, amplitude, pulse duration, the on-duration, and the off-duration may be adjusted based on a response of the BAT temperature as measured by BAT temperature sensor 110. As an example, in response to a rate of BAT temperature increase less than a BAT temperature rate of increase threshold during delivery of DBS, the frequency of the DBS may be increased, the pulse duration may be decreased, the amplitude may be increased, and/or the on-duration may be increased. Additionally, in some examples, other physiological parameters such as skin temperature, heart rate, blood pressure, and expired CO.sub.2 may be monitored via various sensors and used to adjust DBS stimulation parameters.

Additionally, DBS stimulation may be adjusted in response to signals received from other monitoring systems included within DBS system 100 or in communication with DBS system 100. For example, DBS stimulation parameters may be adjusted based on signals received from an activity monitoring system, e.g., adjusted based on presumed metabolic activity of daily living and/or exercise as determined by the activity monitoring system. As another example, DBS stimulation parameters may be adjusted based on signals received from a glucose monitoring system. For example, in response to an increase in blood glucose levels, DBS may be increased in order to elevate BAT expression thereby potentially decreasing hyperglycemia conditions for treatment of diabetes. Additionally, during some conditions, DBS parameters may be adjusted by a clinician, e.g., based on the patient's weight loss, blood pressure, or other metabolic parameters, within safety ranges established a priori.

At 636, method 600 includes determining if exit conditions are met. Exit conditions may comprise any suitable condition for deactivating DBS treatment. For example, exit conditions may include an activation of a fail-safe mechanism of the pulse generator, receiving input from a user via an external device to deactivate DBS treatment, a predetermine time duration having elapsed, etc. If exit conditions are not met at 636, method 600 proceeds back to 626 to continue closed loop control of DBS based on BAT temperature sensor measurements. However, if exit conditions are met at 636, then method 600 proceeds to 638 to discontinue DBS treatment. For example, DBS treatment may be terminated and a flag may be set in a memory component in the pulse generator.

In some embodiments, the above described methods and processes may be tied to a computing system, including one or more computers. In particular, the methods and processes described herein, e.g., method 600 described above, may be implemented as a computer application, computer service, computer API, computer library, and/or other computer program product.

Figure 7:
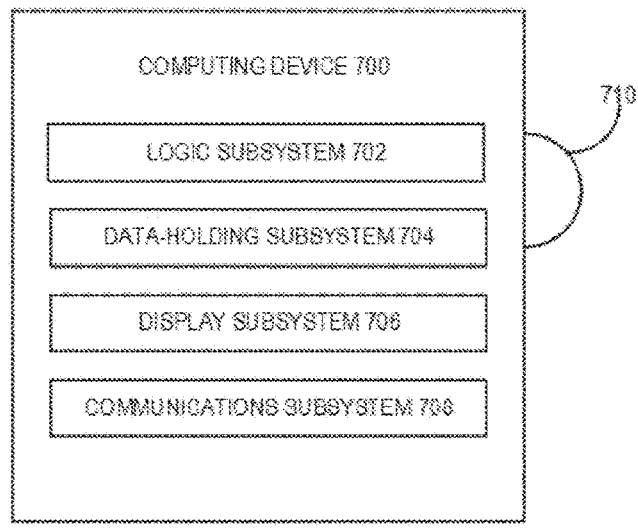
FIG. 7 schematically shows an example computing system in accordance with the disclosure.

FIG. 7 schematically shows a non-limiting computing device 700 that may perform one or more of the above described methods and processes. For example, FIG. 7 may represent controller 128 and/or one or more external devices or systems 222. Computing device 700 is shown in simplified form. It is to be understood that virtually any computer architecture may be used without departing from the scope of this disclosure. In different embodiments, computing device 700 may take the form of a microcomputer, an integrated computer circuit, microchip, a mainframe computer, server computer, desktop computer, laptop computer, tablet computer, home entertainment computer, network computing device, mobile computing device, mobile communication device, gaming device, etc.

Computing device 700 includes a logic subsystem 702 and a data-holding subsystem 704. Computing device 700 may optionally include a display subsystem 706 and a communication subsystem 708, and/or other components not shown in FIG. 7. Computing device 700 may also optionally include user input devices such as manually actuated buttons, switches, keyboards, mice, game controllers, cameras, microphones, and/or touch screens, for example.

Logic subsystem 702 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 704 may include one or more physical, non-transitory, devices configured to hold data and/or instructions executable by the logic subsystem to implement the herein described methods and processes. When such methods and processes are implemented, the state of data-holding subsystem 704 may be transformed (e.g., to hold different data).

Data-holding subsystem 704 may include removable media and/or built-in devices. Data-holding subsystem 704 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 704 may include devices with one or more of the following characteristics: volatile, nonvolatile, dynamic, static, read/write, read-only, random access, sequential access, location addressable, file addressable, and content addressable. In some embodiments, logic subsystem 702 and data-holding subsystem 704 may be integrated into one or more common devices, such as an application specific integrated circuit or a system on a chip.

FIG. 7 also shows an aspect of the data-holding subsystem in the form of removable computer-readable storage media 710, which may be used to store and/or transfer data and/or instructions executable to implement the herein described methods and processes. Removable computer-readable storage media 710 may take the form of CDs, DVDs, HD-DVDs, Blu-Ray Discs, EEPROMs, flash memory cards, and/or floppy disks, among others.

When included, display subsystem 706 may be used to present a visual representation of data held by data-holding subsystem 704. As the herein described methods and processes change the data held by the data-holding subsystem, and thus transform the state of the data-holding subsystem, the state of display subsystem 706 may likewise be transformed to visually represent changes in the underlying data. Display subsystem 706 may include one or more display devices utilizing virtually any type of technology. Such display devices may be combined with logic subsystem 702 and/or data-holding subsystem 704 in a shared enclosure, or such display devices may be peripheral display devices. In some embodiments, computing device 700 may additionally include an audio and/or haptic subsystem including one or more speakers or vibration components which may be used to present audio and/or haptic representations of data held by data-holding subsystem 704.

When included, communication subsystem 708 may be configured to communicatively couple computing device 700 with one or more other computing devices. Communication subsystem 708 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing device 700 to send and/or receive messages to and/or from other devices via a network such as the Internet.

Figure 8:
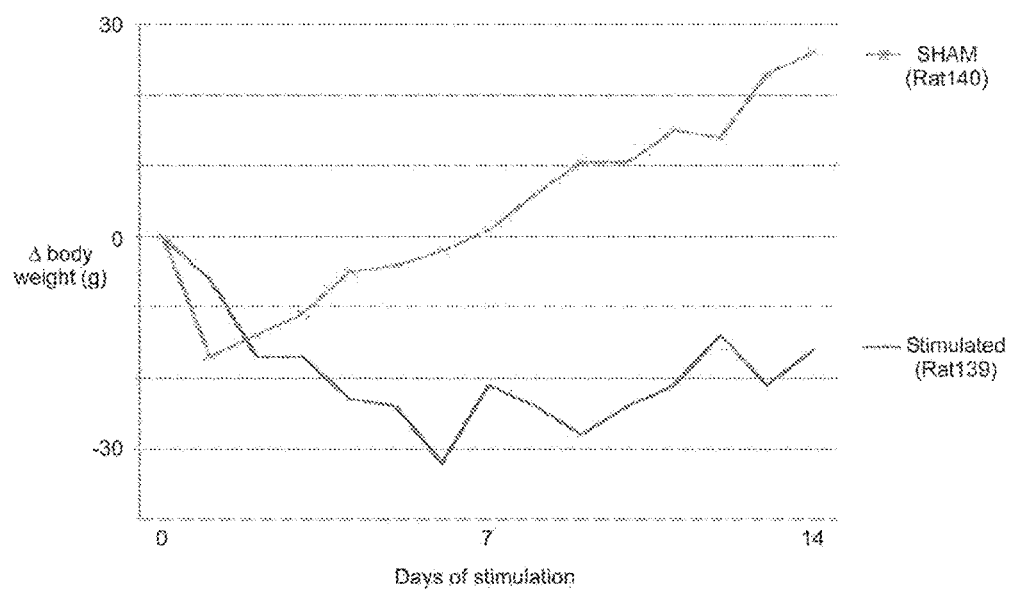
FIG. 8 is a bar graph of feeding efficiency in a group of rats treated and untreated (as indicated) with deep brain stimulation using the disclosed methods.

FIG. 8 shows the change in body weight over two weeks for two diet-induced obese rats. In each rat, an electrode was implanted in the paraventricular hypothalamus (PVH) using both stereotaxic coordinates and increases in brown adipose tissue temperature (TBAT) for site verification. The stimulated rat (Rat139) received stimulation in the PVH over the two week period. The sham treated rat (Rat140) did not receive any stimulation. The data demonstrate the feasibility of the deep brain stimulation using the disclosed methods to elicit weight loss.

Figure 9:
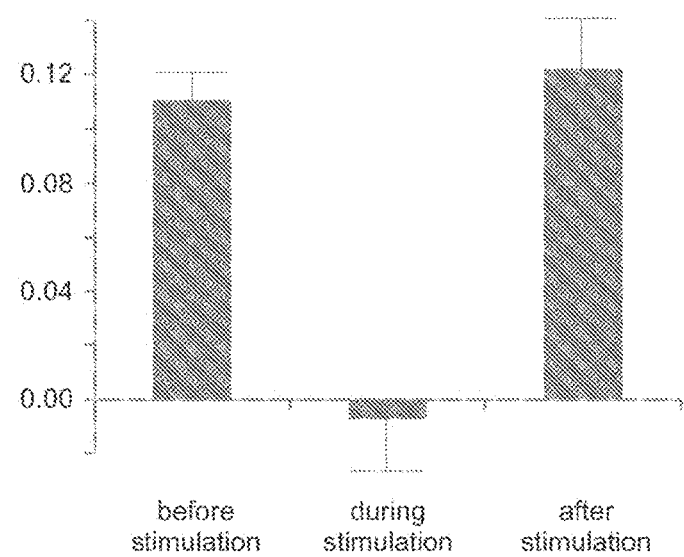
FIG. 9 is a plot showing weight gain in a rat treated with deep brain stimulation using the disclosed methods in comparison to a sham treated rat.

FIG. 9 shows the results of feeding efficiency in rats. Feeding efficiency is defined as grams of body weight gained per gram of food eaten. Rats were implanted with electrodes as described in the description of FIG. 8 above. Feeding efficiency was determined during periods when the deep brain stimulation pulse generator was turned on (during stimulation, n=4) and when the pulse generator was turned off (before stimulation n=4, after stimulation n=2). Although stimulation did not affect the amount of food eaten, the amount of body weight gained per gram of food eaten was reduced during stimulation. These data indicate a significant increase in energy metabolism during periods with deep brain stimulation.

Figure 10:
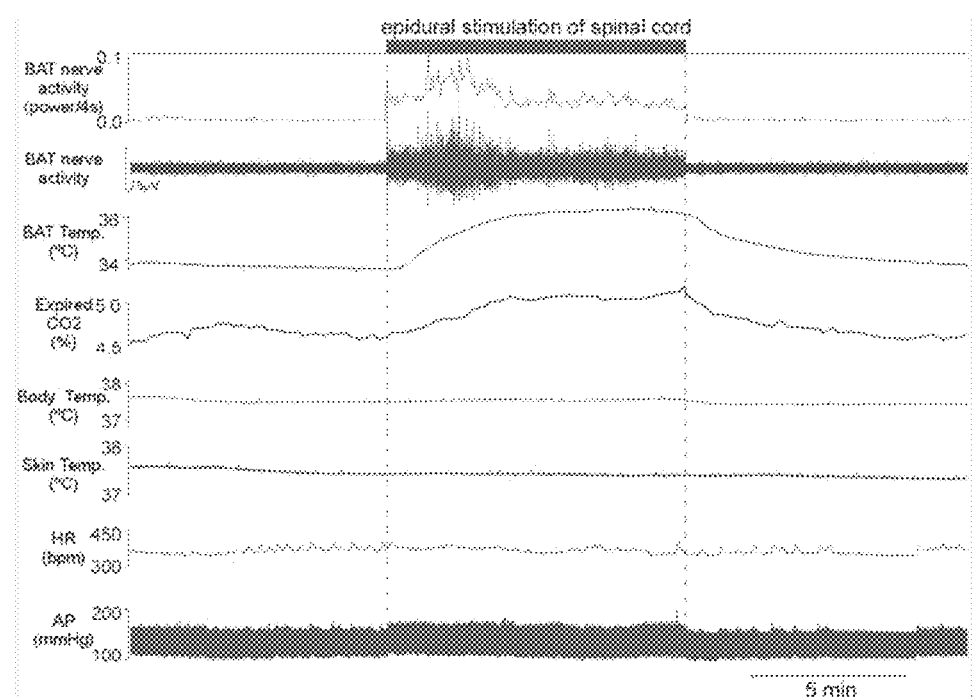
FIG. 10 is a plot showing of data obtained from an anesthetized, paralyzed and ventilated rat for integrated brown adipose tissue (BAT) sympathetic nerve activity (power/4 s), actual BAT sympathetic nerve activity ($\mu V$), BAT temperature (Temp., ° C.), expired $CO_2$(%), core body temperature (° C.), skin temperature (° C.), heart rate (HR, beats per min), and arterial blood pressure (AP, mmHg).

The data shown in FIG. 10 demonstrates the ability to strongly activate metabolism, and thermogenesis in BAT by bilateral epidural stimulation (600 mA, 1 ms, 1 Hz) of the upper thoracic spinal cord. The rat was briefly anesthetized with isoflurane (2% in 100% $O_2$) and the femoral artery, femoral vein, and trachea were cannulated. The rat was transitioned to urethane (0.75 g/kg, intravenous) and α-chloralose (60 mg/kg, intravenous) anesthesia. Arterial blood pressure (AP) and heart rate (HR) were recorded by a pressure transducer connected to the arterial catheter. The rat was maintained at a core body temperature of 37.5±0.5° C. (assessed by a thermocouple placed in the rectum) by perfusing warm water through a thermal blanket that was wrapped around the trunk of the animal. Skin temperature was monitored under the thermal blanket with a thermocouple taped to the rear flank of the rat. The animal was placed in a stereotaxic apparatus with a spinal clamp on the caudal thoracic vertebra (T9-T10). A needle thermocouple was placed into the left brown adipose tissue (BAT) pad to record BAT temperature. The animal was paralyzed with d-tubocurarine (0.6 mg iv) and ventilated with 100% $O_2$ (70 cycles per minute, tidal volume 3.5 ml). Mixed expired $CO_2$ was measured with a capnometer. BAT sympathetic nerve activity was recorded from the central cut end of a small nerve bundle isolated from the ventral surface of the right interscapular BAT pad. Using bipolar hook electrodes under mineral oil nerve activity was filtered (1-300 Hz), amplified (×10,000) and recorded. The muscles over the second, third, and forth thoracic vertebra were retracted and a stimulating electrode (anode) was inserted between second and third vertebra into the epidural space lateral to the spinal cord. A second electrode (cathode) was inserted into the muscle just lateral to the vertebral column. Stimuli were delivered by passing constant current (600 µA) square wave pulses (1 ms duration, 1 Hz frequency) for 10 minutes.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and non-obvious combinations and subcombinations of the various processes, systems and configurations, and other features, functions, acts, and/or properties disclosed herein, as well as any and all equivalents thereof. which the disclosure belongs. Although any methods and materials similar to or equivalent to those described herein can be used in the practice or testing of the present disclosure, the preferred methods and materials are described below.

What is claimed is:

1. A method for placement of a spinal cord stimulation electrode and regulation of spinal cord stimulation in a patient, comprising:
   initially inserting a spinal cord stimulation electrode in a spinal cord region;
   delivering spinal cord stimulation directly via the spinal cord stimulation electrode directly to a first location in a target region of the spinal cord by positioning the spinal cord stimulation electrode in the first location in the target region in response to the initial insertion of the spinal cord stimulation electrode to the first location in the target region;
   receiving temperature measurements from a brown adipose tissue temperature sensor;
   in response to an increasing brown adipose tissue temperature condition, outputting an indication to secure the spinal cord stimulation electrode for delivery of spinal cord stimulation directly to the first location; and
   in response to a non-increasing brown adipose tissue temperature condition, outputting an indication to adjust the spinal cord stimulation electrode by positioning the spinal cord stimulation electrode in an adjusted location in the target region until an increasing brown adipose tissue temperature condition occurs during delivery of spinal cord stimulation directly to the adjusted location in the target region, and then outputting an indication to secure the spinal cord stimulation electrode for delivery of spinal cord stimulation directly to the adjusted location.

2. The method of claim 1, wherein the spinal cord region is selected from spinal intermediolateral nucleus, dorsolateral funiculus, and dorsal horn.

3. The method of claim 1, further comprising delivering spinal cord stimulation directly to the target region via the spinal cord stimulation electrode when the brown adipose tissue temperature is less than a predetermined brown adipose tissue temperature threshold and discontinuing delivery of spinal cord stimulation to the target region via the spinal cord stimulation electrode when the brown adipose tissue temperature is greater than or substantially equal to the predetermined brown adipose tissue temperature threshold.

4. The method of claim 3, wherein delivering spinal cord stimulation comprises delivering, via the spinal cord stimulation electrode, electrical impulses directly to the target region.

5. The method of claim 4, wherein the electrical impulses comprise a predetermined frequency, a predetermined amplitude, and a predetermined pulse duration and are successively delivered for an on-duration and discontinued for an off-duration.

6. The method of claim 5, further comprising adjusting one or more of the frequency, amplitude, pulse duration, the on-duration, and the off-duration based on a response of the brown adipose tissue temperature.

7. The method of claim 5, further comprising adjusting one or more of the frequency, amplitude, pulse duration, the on-duration, and the off-duration based on data received from an activity monitoring system and/or a glucose monitoring system.

8. The method of claim 3, further comprising receiving core temperature measurements via the spinal cord stimulation electrode and, in response to the core temperature increasing above a core temperature threshold, discontinuing delivery of spinal cord stimulation via the electrode until the core temperature falls below the core temperature threshold.

9. The method of claim 1, wherein the target region of the spinal cord comprises a structure associated with metabolism.

10. The method of claim 1, wherein the brown adipose tissue temperature sensor is located on or near a supraclavicular area of the patient.

11. The method of claim 1, wherein the increasing brown adipose tissue temperature condition comprises an increase in brown adipose tissue temperature for a predetermined duration.

12. The method of claim 1, wherein the increasing brown adipose tissue temperature condition comprises an increase in brown adipose tissue temperature compared to a predetermined brown adipose tissue temperature threshold.

13. The method of claim 1, wherein the non-increasing brown adipose tissue temperature condition comprises a decrease in brown adipose tissue temperature for a predetermined duration.

14. The method of claim 1, wherein the spinal cord stimulation electrode comprises a thermode and wherein delivering spinal cord stimulation to the target region comprises cooling the target region via the thermode.

15. The method of claim 1, wherein the spinal cord stimulation electrode is used in the treatment of one or more of obesity, hypertension, diabetes, and hyperglycemia.

16. The method of claim 1, further comprising, in response to a non-increasing brown adipose tissue temperature condition, adjusting operational parameters of the electrode until an increasing brown adipose tissue temperature condition occurs during delivery of spinal cord stimulation to an adjusted location in the target region.

17. The method of claim 16, wherein the operational parameters comprise an activation configuration of electrode contacts.

18. A spinal cord stimulation system, comprising:
an implantable pulse generator, the pulse generator comprising:
an implantable housing;
a battery within the housing; and
a controller within the housing;
an electrode coupled to the pulse generator; and
a supraclavicular brown adipose tissue temperature sensor coupled to the pulse generator;
wherein the controller is configured to:
deliver spinal cord stimulation directly via the electrode to a first location in a target region of the spinal cord in response to an initial insertion of the electrode to the first location by positioning the electrode in the first location in the target region of the spinal cord in response to the initial insertion of the electrode to the target region;
receive temperature measurements from the supraclavicular brown adipose tissue temperature sensor;
in response to an increasing brown adipose tissue temperature condition, output an indication to secure the electrode for delivery of spinal cord stimulation directly to the first location; and
in response to a non-increasing brown adipose tissue temperature condition, output an indication to adjust the electrode by positioning the electrode in an adjusted location in the target region until an increasing brown adipose tissue temperature condition occurs.

19. The system of claim 18, wherein the controller is further configured to deliver spinal cord stimulation via the electrode directly to the target region when temperature measurements from the brown adipose tissue temperature sensor are less than a predetermined brown adipose tissue temperature threshold and discontinue delivery of spinal cord stimulation directly to the target region via the electrode when temperature measurements from the brown adipose tissue temperature sensor are greater than or substantially equal to the predetermined brown adipose tissue temperature threshold.

20. The system of claim 18, wherein the electrode includes a temperature sensing component, and the controller is further configured to receive core temperature measurements from the temperature sensing component of the electrode and, in response to the core temperature measurements increasing above a core temperature threshold, discontinue delivery of spinal cord stimulation to the target region via the electrode until the core temperature measurements fall below the core temperature threshold.

* * * * *

UNITED STATES PATENT AND TRADEMARK OFFICE
CERTIFICATE OF CORRECTION

Page 1 of 1

PATENT NO. : 10,363,421 B2
APPLICATION NO. : 15/943492
DATED : July 30, 2019
INVENTOR(S) : Burchiel et al.

It is certified that error appears in the above-identified patent and that said Letters Patent is hereby corrected as shown below:

In the Specification

Column 1, Line 18, please add "GOVERNMENT INTERESTS - This invention was made with government support under NS040987 and TR000128 awarded by the National Institutes of Health. The government has certain rights in the invention."

Signed and Sealed this
First Day of June, 2021

Drew Hirshfeld
*Performing the Functions and Duties of the*
*Under Secretary of Commerce for Intellectual Property and*
*Director of the United States Patent and Trademark Office*